United States Patent [19]

Manzer et al.

[11] Patent Number: 4,766,260
[45] Date of Patent: Aug. 23, 1988

[54] GAS-PHASE FLUORINATION PROCESS

[75] Inventors: Leo E. Manzer; V. N. Mallikarjuna Rao, both of Wilmington, Del.

[73] Assignee: E. I. du Pont de Nemours and Company, Wilmington, Del.

[21] Appl. No.: 70,826

[22] Filed: Jul. 7, 1987

[51] Int. Cl.$^4$ ............ C07C 17/20; C07C 19/045; C07C 19/05; C07C 19/08
[52] U.S. Cl. .................................................. 570/168
[58] Field of Search ........................................ 570/168

[56] References Cited

U.S. PATENT DOCUMENTS

| | | | |
|---|---|---|---|
| 2,669,590 | 2/1954 | Miller et al. | 570/168 |
| 2,744,147 | 5/1956 | Milks | 570/168 |
| 2,744,148 | 5/1956 | Ruh et al. | 570/168 |
| 3,258,500 | 6/1966 | Swamer et al. | 260/653.7 |
| 3,607,955 | 9/1971 | Gardner | 570/168 |
| 3,650,987 | 3/1972 | Vecchio et al. | 570/168 |
| 3,752,850 | 8/1973 | Scherer et al. | 570/168 |
| 3,755,477 | 8/1973 | Firth et al. | 260/653.4 |
| 3,787,331 | 1/1974 | Groppelli et al. | 570/168 |
| 3,793,229 | 2/1974 | Groppelli et al. | 570/168 |
| 3,803,241 | 4/1974 | Stolkin et al. | 570/168 |
| 4,147,733 | 4/1979 | Fiske et al. | 570/168 |

FOREIGN PATENT DOCUMENTS

| | | | |
|---|---|---|---|
| 1196345 | 11/1985 | Canada . | |
| 1246703 | 8/1967 | Fed. Rep. of Germany | 570/168 |
| 805503 | 12/1958 | United Kingdom | 570/168 |
| 1000083 | 8/1965 | United Kingdom | 570/168 |
| 1000485 | 8/1965 | United Kingdom . | |
| 1070929 | 6/1967 | United Kingdom | 570/168 |

*Primary Examiner*—J. E. Evans
*Attorney, Agent, or Firm*—James E. Shipley

[57] ABSTRACT

An improved gas-phase process for the manufacture of 1,1,1-trifluorodichloroethane and 1,1,1,2-tetrafluorochloroethane by contacting a suitable tetrahaloethylene with hydrogen fluoride in the presence of a selected metal on a high fluorine content alumina support, the reaction being conducted under controlled conditions whereby the production of pentafluoroethane is minimized.

8 Claims, No Drawings

GAS-PHASE FLUORINATION PROCESS

FIELD OF THE INVENTION

An improved process for the manufacture of 1,1,1-trifluorodichloroethane (FC-123) and 1,1,1,2-tetrafluorochloroethane (FC-124), more particularly, a gas-phase reaction of a suitable tetrahaloethylene with hydrogen fluoride in the presence of a selected metal on a high fluorine content alumina support, the reaction being conducted under controlled conditions whereby the production of pentafluoroethane is minimized.

BACKGROUND OF THE INVENTION

Canadian Pat. No. 1,196,345 (1985) describes a process for the preparation of $CF_3CHXY$ (X=H, F; Y=H, F, Cl, Br, I) by addition of HF to the corresponding ethylene in the presence of chromium oxyfluoride at 20°–200° C., expecially 60°–180° C.

U.S. Pat. No. 3,755,477 describes a process for producing fluorinated aliphatic hydrocarbons which comprises fluorinating a halogenated aliphatic hydrocarbon, including tetrachloroethylene and chlorotrifluoroethylene, by reaction in the gas phase with hydrogen fluoride in the presence of a steam-treated and calcined chromium oxide catalyst prepared by a multi-step process. Example 23, col. 5, shows tetrachloroethylene as a raw material with formation of $CF_3CHCl_2$ (20%), $CF_3CHClF$ (20%), $CF_3CHF_2$ (30%), and $CF_3CClF_2$ (20%) at 10/1 $HF/C_2Cl_4$ mol ratio, 5.4 seconds contact time and 360° C. reaction temperature. Example 24, col. 5, shows chlorotrifluoroethylene as a raw material with formation of $CF_2=CF_2$ (20%) and $CF_3CHClF$ (13%) at 1.8/1 $HF/C_2ClF_3$ mol ratio, 4 seconds contact time and 320° C. reaction temperature. In these examples, less desirable pentafluorinated products are obtained in a greater amount than the desired tri- and tetrafluoro products.

U.S. Pat. No. 3,258,500 describes a process for the catalytic vapor phase reaction of HF with halohydrocarbons, including tetrachloroethylene including chlorotrifluoroethylene, employing a catalyst that consists essentially of a heat-activated anhydrous chromium (III) oxide which may be supported on alumina. This catalyst is highly active. Example 17, col. 14, shows fluorination of tetrachloroethylene with this catalyst, like that of the above '477 patent, produces large quantities of the less desirable highly fluorinated pentafluoroethane. At 400° C. the product distribution is 35.0% pentafluoroethane, 9.2% 1-chloro-1,2,2,2-tetrafluoroethane, and 3.5% 1,1-dichloro-2,2,2-trifluoroethane. At 300° C. the product distribution is 38.3% 1-chloro-1,2,2,2-tetrafluoroethane, 25.4% pentafluoroethane, and 16.0% 1,1-dichloro-2,2,2-trifluoroethane. Example 20, col. 15, shows chlorotrifluoroethylene yields $CF_3CHF_2$ as the major product at 400° C.

GB No. 1,000,485 describes a process for the preparation of organic fluorinated compounds by fluorination of halo-olefins in the gaseous phase and at a temperature preferably within the range 200° C. to 400° C. The catalyst consists essentially of partially fluorinated alumina impregnated with one or more polyvalent metal halides. The polyvalent metal may be chromium, cobalt, nickel, or manganese. The total content of polyvalent metal halide expressed as oxide is not more than 15% by weight of the partially fluorinated (70–80%) alumina expressed as alumina. Example 4, (Table 4) shows reaction of tetrachloroethylene with HF over such catalyst yields $CF_3CHCl_2$ as the major product at 220°–290° C. In addition, the patent states that if fluorination of the catalyst is excessive, the activity of the catalyst is impaired (page 3, column 2, lines 85–87).

The references do not disclose how to produce selectively both 1,1,1-trifluorochloroethane and 1,1,1,2-tetrafluorochloroethane while minimizing the production of the pentafluoroethanes, especially at high tetrahaloethylene conversions.

The process of the instant invention achieves the desired high degree of selectivity by minimizing the formation of the pentafluoroethane, through catalyst selection and control of the reaction variables as discussed below and illustrated in the Examples.

SUMMARY OF THE INVENTION

What has been discovered is a process for the preparation of 1,1,1-trifluorodichloroethane and 1,1,1,2-tetrafluorochloroethane by fluorination of a tetrahaloethylene, $C_2Cl_{4-x}F_x$, wherein x=0 to 3, comprising contacting in the gaseous phase at about 300° C. to about 450° C. said tetrahaloethylene and HF with a catalyst comprising a metal in an oxidation state greater than zero, said metal selected from the group consisting of chromium, manganese, nickel, and cobalt, and mixtures thereof, on a support consisting essentially of aluminum, oxygen, and fluorine in such proportions that the fluorine content corresponds to an $AlF_3$ content of at least 90% by weight of the catalyst composition exclusive of the metal, said $AlF_3$ content being obtained by pretreatment with HF.

DETAILS OF THE INVENTION

The tetrahaloethylene of this invention defined by the formula $C_2Cl_{4-x}F_x$, wherein x=0 to 3, includes $CCl_2=CCl_2$, $CClF=CCl_2$, $CClF=CClF$, $CF_2=CCl_2$, and $CF_2=CClF$, and mixtures of these. Tetrachloroethylene is preferred.

By a high fluorine content alumina support is meant a composition comprising aluminum, oxygen and fluorine in such proportions that the total fluorine content of the catalyst composition taken as $AlF_3$ corresponds to at least 90 weight percent, exclusive of the supported metal, preferably 95 weight percent $AlF_3$ or more.

The remainder of the support may include alumina or aluminum oxyfluoride. The high $AlF_3$ content support can be prepared in-situ by exhaustive fluorination of alumina impregnated with at least one chromium, manganese, nickel, or cobalt compound which may be in the form of the oxide, oxyhalide, halide or pseudohalide or such other form which is convertible to the fluoride or oxyfluoride under the conditions of the HF pretreatment step described herein. The halides include fluorides, chlorides, or bromides. The pseudohalides include cyanides, cyanates and thiocyanates. The preferred metals are manganese, nickel and cobalt. The most preferred metal is cobalt.

The total content of chromium, manganese, nickel, or cobalt expressed as the divalent oxide is not more than 20% by weight of the supported catalyst.

The catalyst of the instant invention can be prepared prior to reaction with the tetrahaloethylene, by impregnating $Al_2O_3$ with the desired metal compound and treatment with HF at elevated temperatures until the desired degree of fluorination is obtained, e.g., at about 200 degrees Centigrade to about 450 degrees Centigrade. The treatment with HF can conveniently be done in the reactor which is to be used for contacting tetrachloroethylene with HF.

A suitable catalyst may be prepared, for example, as follows:

A quantity of $Al_2O_3$ is impregnated with a solution of a catalytically effective amount of one or more metal halides or pseudohalides of chromium, manganese, nickel, or cobalt. By catalytically effective amount is meant an amount of the metal expressed as the divalent oxide between about 0.02 to 20 weight percent of the alumina support, preferably 0.1 to 5 weight percent. The impregnated $Al_2O_3$ can be dried until essentially all moisture is removed, e.g., for about 18 hours at about 100° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and HF diluted with $N_2$ is passed through the reactor. The $N_2$ can be gradually reduced until only HF is being passed through the reactor. At this point the temperature can be increased to about 450° C. and held at that temperature to convert the impregnated $Al_2O_3$ to a fluoride content corresponding to at least 90% $AlF_3$, e.g., for 15 to 300 minutes, depending on the HF flow and the catalyst volume.

The reaction of the tetrahaloethylene with HF in the presence of the catalyst of the instant invention is conducted at 300° C. to 450° C., preferably about 300° C. to 400° C., and most preferably about 325° C. to 350° C., with a contact time of about 5 to 100 seconds, preferably about 10 to 90 seconds, and most preferably about 15 to 60 seconds.

The molar ratio of HF to the tetrahaloethylene can range from about 1/1 to 20/1, preferably about 3/1 to 10/1, and most preferably about 4/1 to 7/1.

In general, with a given catalyst composition, the higher the temperature, the greater the HF/tetrahaloethylene mol ratio, and the longer the contact time, the greater is the conversion of the tetrahaloethylene to fluorinated products. The above variables can be balanced, one against the other, so that formation of FC-123 is favored over FC-124 and the production of these two compounds taken together is maximized and that of higher fluorinated products minimized.

A key feature of the invention is that through catalyst selection and process control, as described herein, the desired tri- and tetrafluoro products can be obtained as the major products at high tetrahaloethylene conversions, normally between about 30% and about 90%. Preferably, the reaction variables are controlled so as to keep the production of the pentafluoro product below about 10 area percent, as determined gas chomatographically, of the products produced. Thus, as illustrated in the examples with tetrachloroethylene, the tri- and tetralfluoro products are obtained in very high yields while minimizing the production of higher fluorinated products even at high conversions of tetrachloroethylene.

Intermediates formed during the course of the reaction, such as $CHF_2CClF_2$, $CHClFCClF_2$, $CHCl_2CClF_2$, $CClF=CCl_2$, and $CHCl_2CCl_2F$, can be recycled to the reactor for the production of additional FC123 and FC-124. In addition, FC-123can be recycled to the reactor for the production of additional FC-124 when this is desired.

The reaction of the tetrahaloethylene with HF may be conducted in any suitable reactor, including fixed and fluidized bed reactors. The reaction vessel should be constructed from materials which are resistant to the corrosive effects of hydrogen fluoride such as Hastelloy and Inconel.

Pressure is not critical. Atmospheric and superatmospheric pressures are the most convenient and are therefore preferred.

The fluorinated alkanes produced by the invention have utility as blowing agents and refrigerants. They can also be used as starting materials for the preparation of other useful compounds. For example, FC-124 can be used to prepare 1,1,1,2-tetrafluoroethane.

EXAMPLES

In the following illustrative examples, all parts and percentages are by weight and all temperatures are Centigrade unless otherwise stated. All reactions used commercial HF containing only trace amounts of water.

General Procedure for Fluorination

The reactor (a 0.5 inch ID, 12 inch long Inconel pipe) was charged with the amount of catalyst as described in the following examples, and placed in a sand bath. The bath was gradually heated to 400° while nitrogen gas at a flow rate of 50 ml/minute was passed through the reactor to remove traces of water. The temperature was lowered to 200° and HF and nitrogen gas (1:4 molar ratio) were passed through the reactor and the nitrogen flow was decreased with time until neat HF was being passed through the reactor. At this point, the temperature was gradually raised to 450° and maintained there for 15 to 300 minutes. The fluorine content of the catalyst composition corresponded to an $AlF_3$ content, exclusive of the metal, of at least 95%.

The temperature was then decreased to the indicated values and, thereafter, $CCl_2=CCl_2$ flow was started. The flows of HF and $CCl_2=CCl_2$ were adjusted to give the indicated molar ratios and contact times.

The reactor effluent was scrubbed with aqueous potassium hydroxide to remove HCl and HF and sampled on-line with a Hewlett Packard HP 5890 gas chromatograph using a 20 foot long, one-eighth inch diameter, column containing "Krytox" perfluorinated polyether on an inert support and a helium flow of 35 cc/minute. Gas chromatographic conditions were 70° for 3 minutes followed by temperature programming to 180° at a rate of 6°/minute.

EXAMPLES 1-2

The General Procedure for Fluorination was followed using 19.8 g. (30 cc) of $NiCl_2/Al_2O_3$ (2% $NiCl_2$) as the initial catalyst charge. The results of the reaction of HF with $CCl_2=CCl_2$ over the prepared catalyst are given in Table 1.

TABLE 1

| | Example | |
|---|---|---|
| | 1 | 2 |
| Temp. °C. | 325 | 350 |
| HF/C$_2$Cl$_4$ (mol ratio) | 5/1 | 6/1 |
| Contact Time (sec.) | 45 | 30 |
| Conversion % | 58.7 | 61.2 |
| | Area Percent | |
| CF$_3$CHCl$_2$ | 70.0 | 60.6 |

TABLE 1-continued

| | Example | |
|---|---|---|
| | 1 | 2 |
| $CF_3CHClF$ | 12.4 | 20.3 |
| $CF_3CHF_2$ | 0.5 | 1.3 |
| $CF_3CHCl_2$ plus $CF_3CHClF$ | 82.4 | 80.9 |

EXAMPLES 3-4

The General Procedure for Fluorination was followed using 19.5 g. (30 cc) of $MnCl_2/Al_2O_3$ (1.87% $MnCl_2$) as the initial catalyst charge. The results of the reaction of HF with $CCl_2=CCl_2$ over the prepared catalyst are given in Table 2.

TABLE 2

| | Example | |
|---|---|---|
| | 3 | 4 |
| Temp. °C. | 350 | 375 |
| $HF/C_2Cl_4$ (mol ratio) | 6/1 | 10/1 |
| Contact Time (sec.) | 30 | 25 |
| Conversion % | 70.4 | 61.5 |
| Area Percent | | |
| $CF_3CHCl_2$ | 67.8 | 58.5 |
| $CF_3CHClF$ | 18.5 | 17.6 |
| $CF_3CHF_2$ | 1.0 | 1.1 |
| $CF_3CHCl_2$ plus $CF_3CHClF$ | 86.3 | 76.1 |

EXAMPLES 5-9

The General Procedure for Fluorination was followed using 18.4 g. (30 cc) of $CoCl_2/Al_2O_3$ (2.0% $CoCl_2$) as the initial catalyst charge. The results of the reaction of HF with $CCl_2=CCl_2$ over the prepared catalyst are given in Table 3.

TABLE 3

| | Example | | | | |
|---|---|---|---|---|---|
| | 5 | 6 | 7 | 8 | 9 |
| Temp. °C. | 350 | 350 | 350 | 350 | 350 |
| $HF/C_2Cl_4$ (mol ratio) | 7/1 | 10/1 | 5/1 | 5/1 | 3/1 |
| Contact Time (sec.) | 13.2 | 19.3 | 31.8 | 17.6 | 25.7 |
| Conversion % | 87.3 | 90.3 | 86.8 | 75.7 | 60.0 |
| Area Percent | | | | | |
| $CF_3CHCl_2$ | 56.5 | 52.8 | 53.6 | 57.8 | 52.1 |
| $CF_3CHClF$ | 37.2 | 41.1 | 39.4 | 32.2 | 32.9 |
| $CF_3CHF_2$ | 1.6 | 2.1 | 2.2 | 1.5 | 2.5 |
| $CF_3CHCl_2$ plus $CF_3CHClF$ | 93.7 | 93.9 | 93.0 | 90.0 | 85.0 |

EXAMPLES 10-13

The General Procedure for Fluorination was followed using 20.4 g. (30 cc) of $CrCl_3/Al_2O_3$ (5.2% $CrCl_3$ on $Al_2O_3$) as the initial catalyst charge. The results of the reaction of HF with $CCl_2=CCl_2$ over the prepared catalyst are given in Table 4.

TABLE 4

| | Example | | | |
|---|---|---|---|---|
| | 10 | 11 | 12 | 13 |
| Temp. °C. | 425 | 350 | 350 | 350 |
| $HF/C_2Cl_4$ (mol ratio) | 4/1 | 4/1 | 5/1 | 6/1 |
| Contact Time (sec.) | 15 | 60 | 60 | 60 |
| Conversion % | 62.1 | 78.3 | 78.1 | 80.3 |
| Area Percent | | | | |
| $CF_3CHCl_2$ | 31.4 | 50.8 | 49.6 | 46.1 |
| $CF_3CHClF$ | 22.2 | 28.5 | 29.7 | 33.3 |
| $CF_3CHF_2$ | 9.8 | 6.9 | 7.3 | 7.2 |
| $CF_3CHCl_2$ plus $CF_3CHClF$ | 53.6 | 79.3 | 79.3 | 79.4 |

We claim:

1. A process for the preparation of 1,1,1-trifluorodichloroethane and 1,1,1,2-tetrafluorochloroethane by fluorination of a tetrahaloethylene, $C_2Cl_{4-x}F_x$, wherein x=0 to 3, comprising contacting in the gaseous phase at about 300° C. to about 450° C. said tetrahaloethylene and HF with a catalyst comprising at least one metal in an oxidation state greater than zero, said metal selected from the group consisting of chromium, manganese, nickel, and cobalt, on a support consisting essentially of aluminum, oxygen, and fluorine in such proportions that the fluorine content corresponds to an $AlF_3$ content of at least 90% by weight of the catalyst composition exclusive of said metal, said $AlF_3$ content being obtained by pretreatment of alumina with HF.

2. The process of claim 1 wherein the tetrahaloethylene is tetrachloroethylene.

3. The process of claim 1 wherein the catalyst contains about 0.02 to about 20 weight percent of said metal expressed as the divalent oxide.

4. The process of claim 1 wherein the catalyst contains about 0.1 to about 5 weight percent of metal said expressed as the divalent oxide.

5. The process as in claims 1, 2, or 3 wherein the HF is contacted with the tetrahaloethylene at a mol ratio of about 1/1 to about 20/1, at a temperature of about 300° C. to about 400° C., and a contact time of about 5 to about 100 seconds.

6. The process of claim 1 wherein said metal is selected from the group consisting of manganese, nickel, and cobalt.

7. The process of claim 4 wherein said metal is cobalt.

8. The process of claim 1 further comprising the step of recycling at least a portion of the $CF_3CHCl_2$ produced to the contacting step for conversion to additional $CF_3CHClF$.

* * * * *